United States Patent
Vezzetti et al.

(10) Patent No.: US 12,089,987 B2
(45) Date of Patent: Sep. 17, 2024

(54) COMPUTER BASED METHOD FOR CLASSIFYING A MASS OF AN ORGAN AS A CYST

(71) Applicant: POLITECNICO DI TORINO, Turin (IT)

(72) Inventors: Enrico Vezzetti, Turin (IT); Federica Marcolin, Turin (IT); Antonio Froio, Turin (IT); Federica Gerace, Turin (IT); Luca Bonacina, Turin (IT); Daniele Conti, Turin (IT); Andrea Cesari, Turin (IT); Rosilari Bellacosa Marotti, Turin (IT)

(73) Assignee: POLITECNICO DI TORINO, Turin (IT)

( * ) Notice: Subject to any disclaimer, the term of this patent is extended or adjusted under 35 U.S.C. 154(b) by 395 days.

(21) Appl. No.: 17/615,102

(22) PCT Filed: May 28, 2020

(86) PCT No.: PCT/IB2020/055058
§ 371 (c)(1),
(2) Date: Nov. 30, 2021

(87) PCT Pub. No.: WO2020/240455
PCT Pub. Date: Dec. 3, 2020

(65) Prior Publication Data
US 2022/0230325 A1    Jul. 21, 2022

(30) Foreign Application Priority Data
May 31, 2019    (IT) .................. 102019000007806

(51) Int. Cl.
*A61B 8/08*    (2006.01)
*G06T 7/00*    (2017.01)
(Continued)

(52) U.S. Cl.
CPC .......... *A61B 8/085* (2013.01); *A61B 8/5223* (2013.01); *G06T 7/0012* (2013.01); *G06T 7/11* (2017.01);
(Continued)

(58) Field of Classification Search
CPC ..... A61B 8/085; A61B 8/5223; G06T 7/0012; G06T 7/11; G06T 7/12; G06T 7/60;
(Continued)

(56) References Cited

U.S. PATENT DOCUMENTS

| | | | |
|---|---|---|---|
| 5,984,870 A * | 11/1999 | Giger | G06T 7/0012 600/443 |
| 6,858,007 B1 | 2/2005 | Akselrod et al. | |
| 2019/0343490 A1 * | 11/2019 | White | A61B 8/5276 |

FOREIGN PATENT DOCUMENTS

WO    2019005722 A1    1/2019

OTHER PUBLICATIONS

Timmerman, "The use of mathematical models to evaluate pelvic masses; can they beat an expert operator?" (published in Best Practice & Research Clinical Obstetrics and Gynaecology, vol. 18, No. 1, pp. 91-104, 2004).*

(Continued)

*Primary Examiner* — Casey L Kretzer
(74) *Attorney, Agent, or Firm* — Bayramoglu Law Offices LLC

(57) ABSTRACT

A computer based method for classifying a mass of an organ such as a cyst is provided. The computer based method provides a class indicating a presence of a serum and a solid in the cyst and a subclass indicating a presence of one or more serous loculi or one or more solid loculi in the cyst. The computer based method is advantageous applications for a diagnosis of ovarian cysts.

11 Claims, 6 Drawing Sheets

(51) Int. Cl.
  *G06T 7/11* (2017.01)
  *G06T 7/12* (2017.01)
  *G06T 7/60* (2017.01)

(52) U.S. Cl.
  CPC .................. *G06T 7/12* (2017.01); *G06T 7/60* (2013.01); *G06T 2207/10132* (2013.01); *G06T 2207/20081* (2013.01); *G06T 2207/20084* (2013.01); *G06T 2207/30096* (2013.01)

(58) Field of Classification Search
  CPC . G06T 2207/10132; G06T 2207/20081; G06T 2207/20084; G06T 2207/30096
  See application file for complete search history.

(56) References Cited

OTHER PUBLICATIONS

Yair Zimmer, et al., An Automatic Approach for Morphological Analysis and Malignancy Evaluation of Ovarian Masses Using B-Scans, Ultrasound in Med. & Biol., 2003, pp. 1561-1570, vol. 29, No. 11.

\* cited by examiner

Unilocular

Solid unilocular

Multilocular

Solid multilocular

Solid

Background

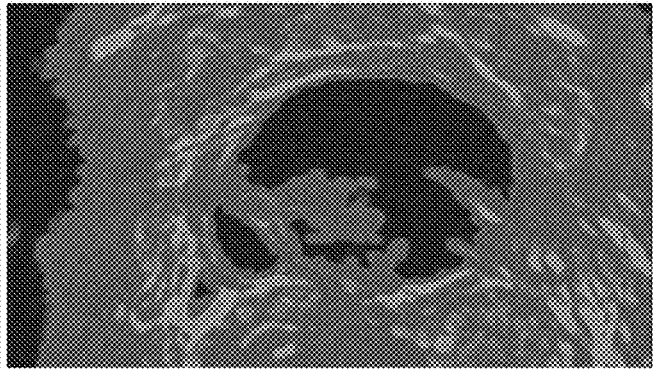
FIG. 6A
FIG. 6B
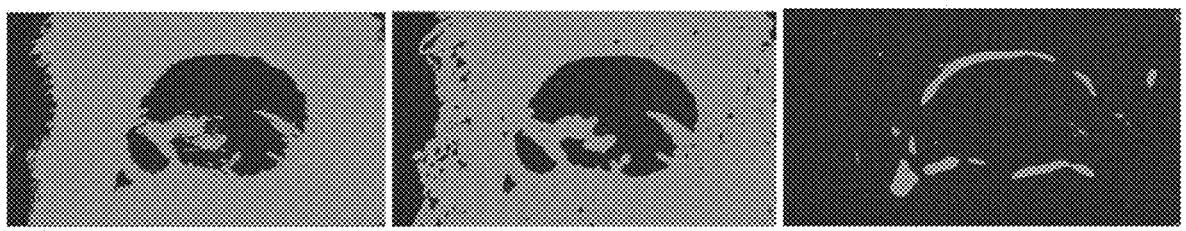
FIG. 7A
FIG. 7B
FIG. 7C

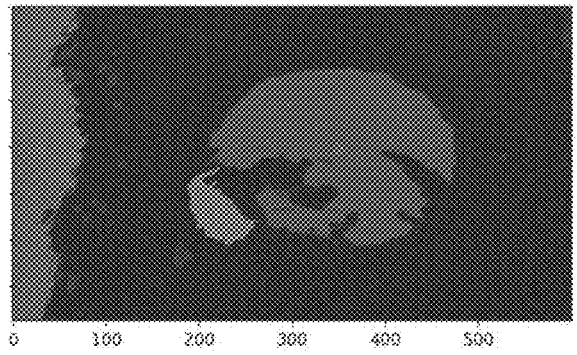 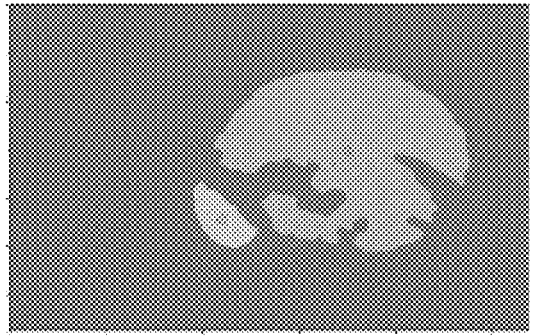
FIG. 8A　　　　　　　　　　　　　　FIG. 8B
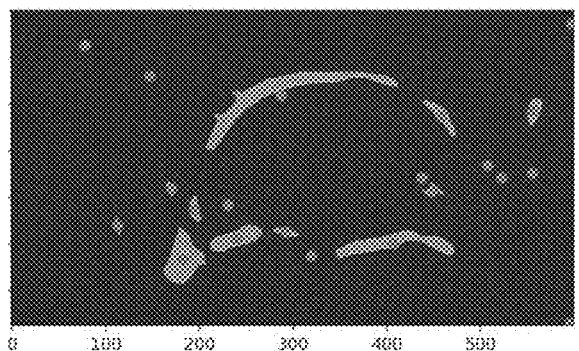 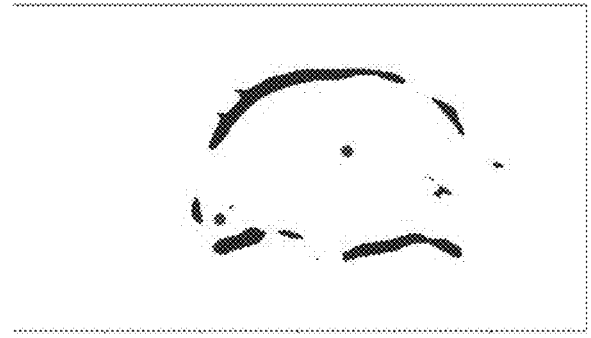
FIG. 9A　　　　　　　　　　　　　　FIG. 9B

COMPUTER BASED METHOD FOR CLASSIFYING A MASS OF AN ORGAN AS A CYST

CROSS REFERENCE TO THE RELATED APPLICATIONS

This application is the national stage entry of International Application No. PCT/M2020/055058, filed on May 28, 2020, which is based upon and claims priority to Italian Patent Application No. 102019000007806 filed on May 31, 2019, the entire contents of which are incorporated herein by reference.

TECHNICAL FIELD

The present invention relates to the field of computer based methodologies for processing ultrasound images of cysts and providing support for diagnosis.

Specifically, the present invention relates to a computer based method for characterizing and classifying masses present in organs of the human body.

BACKGROUND

Ultrasound imaging methods are known for providing data to support the preparation of a diagnosis. There is a need to process data automatically to early detect harmful asymptomatic pathologies, such as an ovarian tumor, and, therefore, normally diagnosed too late for effective and minimally invasive therapy.

SUMMARY

The present invention at least partially solves the drawbacks specified above by means of a computer based method for finding and characterizing an anatomic mass of an organ such as a cyst and providing a class indicating the presence of a serum in the cyst and a subclass indicating the presence of one or more serous loculi in the cyst, the method including the steps of:
(a) obtaining at least an ultrasound image of an examined anatomic entity including the anatomical mass;
(b) using a first algorithm based on a neural network that processes the image to generate the characterization as a cyst and/or the class;
(c) use a second algorithm of computational graphics for:
a. identifying internal regions of the image, in particular a fluid region, for example with low echogenicity, or a boundary region, for example with high echogenicity, of the anatomic mass on the basis of at least two different thresholds applied to a mathematical function of the echogenicity of the image;
ii. classifying the internal region as serous or solid on the basis of at least one quantitative morphological parameter of the internal region and of an aggregation model generating an association between at least one internal region of fluid and an internal boundary region when a proximity condition is verified between the regions; in particular, with reference to the serous classification, a form factor of the internal region and/or a roughness of the boundary of the region and/or a position of the centroid, e.g. center of gravity, and an aggregate with a boundary region having half-axes of a size similar to those of the internal fluid area is identified; with reference to the solid classification, for example the aggregation model provides the association between a fluid area and an outline having respective axes of remarkably different dimensions and it is deduced that the intermediate area between the boundary region and the fluid region is solid.
iii. counting the number of fluid regions such as serous loculi and/or a number of solid regions;
(d) providing a classification comprising the class and subclass based on the combination of outputs of the first and second algorithms.

The main steps of the ultrasound image processing according to the present invention are to recognize whether a cyst is present in the image or not; and identifying morphological or geometric features of the cyst. For example, the cyst may not be present because the ultrasound image shows, for example, an ultrasound image of a healthy ovary or with healthy and non-pathological formations.

The inventors have determined that neural networks are particularly effective at recognizing a cyst regardless of the various types and forms that the latter can take both with respect to a perfectly healthy configuration and in the case of functional and pathological formations. For example, according to a particular non-limiting embodiment, neural networks identify both whether the cyst is present, whether it is serous or solid, and through the imaging algorithms the number of loculi, equal to or greater than one, is identified. In fact, the processing of the geometric parameters of an ultrasound image through known algorithms of computational graphics, in particular based on the delimitation of the contours of the serous areas, easily enable to provide more detailed parameters. The combination in any order of these tools provides a classification and sub-classification useful for the doctor to evaluate any further in-depth examination or diagnose a normal situation.

Furthermore, the method is also applicable by performing the identification through the computational graphics algorithms of the geometric features, such as fluid regions, e.g. serum, blood etc., or solid boundary regions, centroids, minor and major axis of the serous regions; the subsequent calculation of quantitative parameters such as the extension, i.e. the number of pixels, of the serous or boundary regions, the position of centroids, the extension and the inclination with respect to an image reference system and an irregularity index of the edge regions such as roughness in an ultrasound image and subsequently associating the data with the result of the recognition process through neural networks, which allows to associate quantitative data with the actual presence of a cyst or, otherwise, the indication that the image does not include a cyst.

It is also possible, with particular reference to the use of convolutional neural networks, that both classification and sub-classification are generated, without however a quantification of the number of loculi, and the related redundant data with those obtained through the computational graphics algorithms, i.e. solid or serous based on the percentage of serous area with respect to the overall area of the cyst, and unilocular or multilocular, are compared with those obtained by computational graphics algorithms. Preferably, classification and sub-classification are presented as a result of the method of the present invention when the result of the processing through the neural network and that of the computational graphics algorithms agree.

According to a preferred embodiment, the obtaining step comprises the step of obtaining a multiframe clip of ultrasound images of the examined anatomic entity including the anatomic mass; and comprising the step of providing an overall class or sub-class of the clip so that multilocular prevails over unilocular and/or solid prevails over serous when a first subclass of a first frame and a second subclass of a second frame of the clip are different.

The method of the present invention can be applied to individual frames and, subsequently, an overall classification of the anatomical mass of the clip must be provided. Since it is possible that a frame illustrates two loculi and a further frame illustrates a single loculum or provides a serous classification in one frame and a solid classification in another frame, prevalence criteria must be provided so that the method provides a single classification of the anatomic mass in the presence of frames with different classifications.

Further advantageous characteristics will become more evident from the following description of preferred but not exclusive embodiments, provided purely by way of non-limiting example.

BRIEF DESCRIPTION OF THE DRAWINGS

The present invention will be described below by means of some preferred embodiments, given as a non-limiting example, with reference to the attached drawings. These drawings illustrate different aspects and examples of the present invention and, where appropriate, structures, components, materials and/or similar elements in different figures are indicated by similar reference numbers.

FIG. 6A is an ultrasound image and FIG. 6B is the result of applying an entropic filter to the image of FIG. 6A;

FIGS. 7A and 7B are respective binary images through a first and a second slightly different threshold and FIG. 7C is a binarized image by a third threshold of FIG. 6B;

FIGS. 8A and 8B illustrate two subsequent process steps of the image of FIG. 7A, 7B;

FIGS. 9A and 9B illustrate two subsequent process steps of FIG. 7C;

DETAILED DESCRIPTION OF THE EMBODIMENTS

Figure 1A:
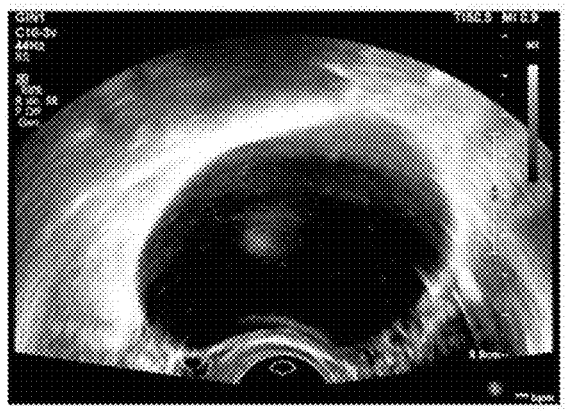
FIGS. 1A-1F are a series of ultrasound images relating to ovarian cysts of different classes.
Figure 1B:
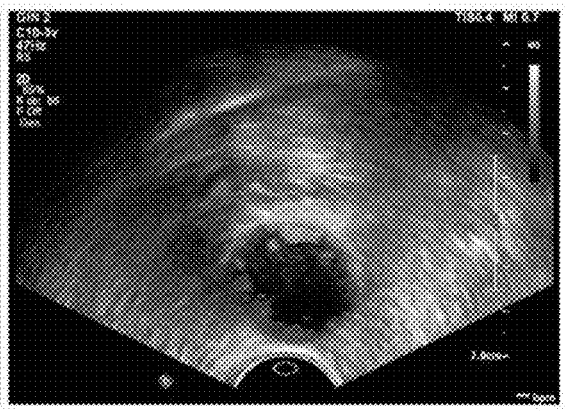
Figure 1C:
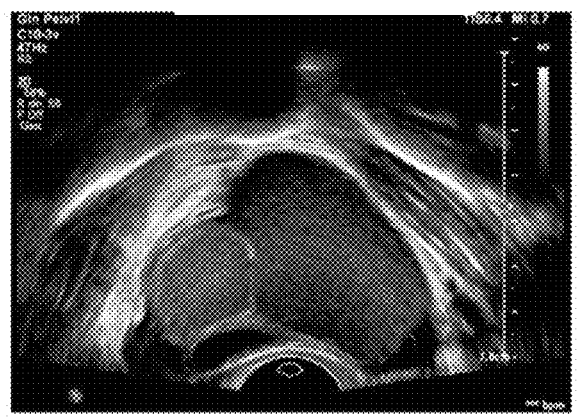
Figure 1D:
Figure 1E:
Figure 1F:
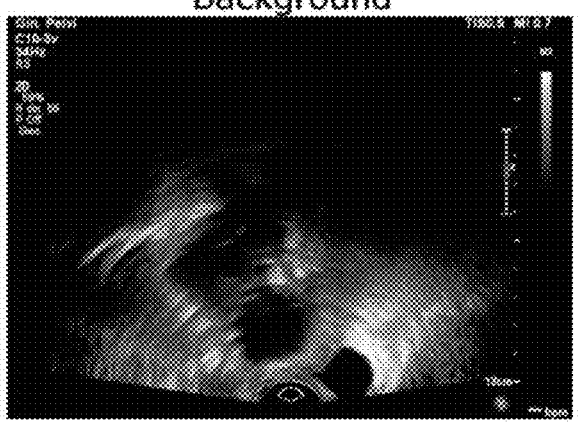

While the invention is susceptible of various modifications and alternative constructions, some preferred embodiments are shown in the drawings and will be described in detail below.

With reference to FIGS. IA-IF, images are shown relating to a non-limiting classification that finds inspiration from the IOTA classification, used to divide ovarian cysts and support a doctor in the diagnosis. It should be noted that this method is also applicable to the recognition and classification of renal and pancreatic cysts.

In greater detail, according to a non-limiting example of classification, a unilocular mass has a single region filled with liquid of various nature, which determines its ecogenicity, i.e. the intensity of echo reflected by the material. A non-ecogenic mass will appear as completely black. A hypoechoic mass will have soft and little diffused grays within the mass itself. An isoechoic mass will present a content which in gray scale will be comparable with the tissues external to the mass. A hyperechoic mass instead will be a particularly bright mass in ultrasound.

In the event that the liquid is serum, the level of echogenicity will be low or not present (see the region below the unilocular mass shown in FIGS. 1A-1F). In the event that there are blood spills or the presence of mucinous masses in the cyst, this will be hypoechoic or at most isoechogenic (see the multilocular mass in FIGS. 1A-1F). The presence of solid masses instead inside the cyst will give it an isoechoic or hyperechoic appearance.

Serum and blood spills are not associated with an important level of risk, while the presence of solid masses is one of the main signs of potential malignancy, even if this is not a direct implication.

By solid mass instead we mean mass that protrudes from the walls of the cyst and whose growth tends to fill the cystic space. If this is greater than 3 mm in height, it is called papilla. In FIGS. 1A-1F the solid unilocular mass has numerous papillae distributed along the entire cystic boundary, which assumes an irregular structure.

A multilocular cyst can have all the characteristics described above, but the cystic space is not unique but divided by septa in multiple chambers. The septum is therefore a portion of tissue that develops through the content of the cyst and divides it into multiple spaces.

Intersections between septa or between septa and a cystic wall are a preferential place for the development of a solid mass and must be adequately monitored.

A mass is instead defined as solid when the solid component has occupied the cystic space for more than 80% of the mass itself; an example of how a computation graphics algorithm can associate binary segments of an image with a cyst is described below to define the overall area of the cyst and calculate the serous percentage. In addition, it is also possible through appropriate training of the neural network, that the latter is able to classify images related to solid or serous unilocular cysts. Basically, the level of risk associated with the mass increases with this classification, starting from a level of less than 1% for a unilocular serum mass, up to a high level of risk for solid masses, that can therefore be defined clear carcinomas.

Lastly, for the frames of clips that cannot be associated with any of the classes described above, a 'miscellaneous' class is preferably associated, for example called background. This therefore does not only include ultrasounds regarding tissues of other organs and completely "gray", but can include areas that recall the cystic shape and echogenicity, such as for example intestinal loops, blood vessels, etc., or transition areas between the cystic mass and the adjacent tissues, therefore regions where the quality of the cystic image would not be high enough to allow the accurate training of the algorithms and would even risk affecting it. In this regard, the background image shown in FIGS. 1A-1F was chosen as representative of the class.

A two-dimensional ultrasound image, whether selected by the operator who performs the ultrasound and stored by means of a special ultrasound function or frame of a stored ultrasound clip, is initially processed to allow a better operation of the method according to the present invention. In particular, the image is cut out around the region of interest (ROI-automatically-identified for example through template matching or through crop/crop based on a frame of pre-set size and position without human intervention) and segmented through global thresholding; both of these steps respectively enable to remove unnecessary parts from the image (in particular the metadata, imprinted as a watermark on the image) and to ease the application of computational graphics algorithms which will be more detailed below.

In addition, the image is processed to reduce speckle noise, i.e. despeckling.

Despeckling is necessary to prevent variations in brightness linked to the phenomenon of sound wave interference from covering or merging with the salient aspects of the image. The chosen filtering is median filtering. Other alternatives are, but are not limited to, algorithms such as anisotropic diffusion or wavelet denoising.

Figure 2:
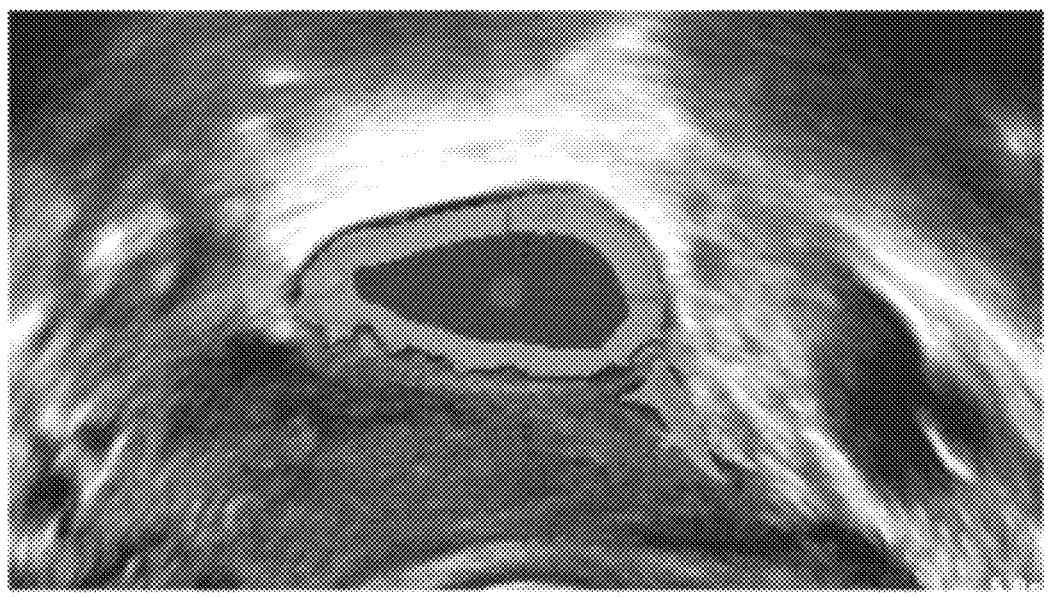
FIG. 2 is an ultrasound image processed for the calculation of a centroid of an internal area of the image.
Figure 3:
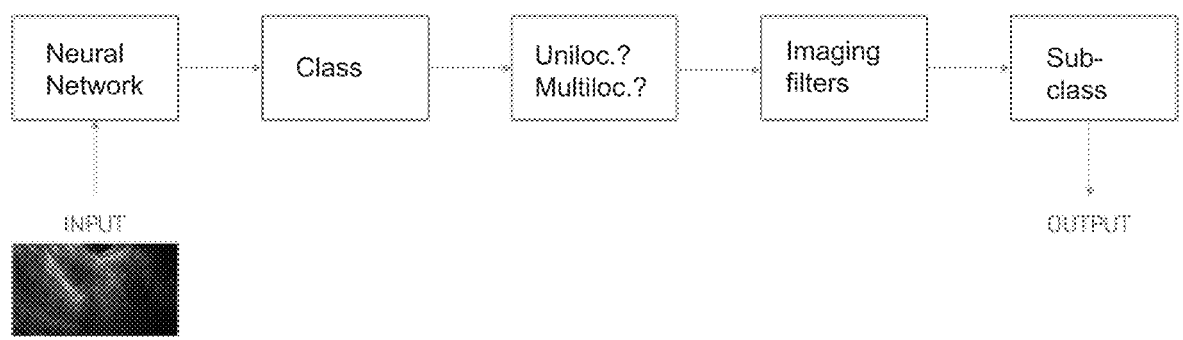
FIG. 3 is a block diagram of the method according to a non-limiting embodiment of the present invention.

A subsequent phase of edge detection has the object of extracting the contours of the region of interest within the image, in order to derive relevant geometric features (cyst area, contours), as shown in a first example in FIG. 2.

In general, it is assumed that the different regions of the ultrasound image are characterized by different levels of entropy: low, in correspondence with uniform areas, such as for example the content of serous cysts, high in correspondence with abrupt variations, typically in correspondence with boundaries. These algorithms will be described in more detail later.

The automatic classification of the main tumor features of the ovary, such as loculi and papillae, is carried out according to the present invention through feed-forward neural networks. A feed-forward network is an acyclic graph, structured in a sequence of layers. This architecture makes the network particularly suitable for performing the role of classifier.

In a classification problem, given a set of objects, such as, for example, several ultrasound images of cysts, the network must be able to place each of them in the respective class, for example to determine if the cyst in a given ultrasound image belongs to the class of unilocular cysts or to that of multiloculars.

Figure 4:
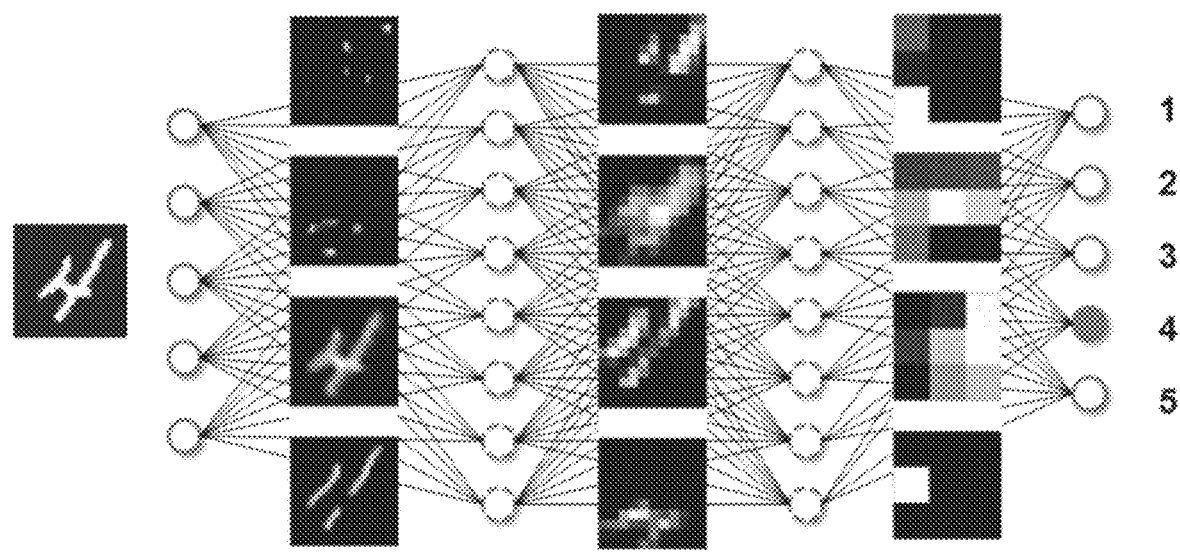
FIG. 4 is a simplified scheme of a neural network used in the method of the present invention.

To accomplish this task, the network generates increasingly abstract and complex representations of the object to be classified along the layers, emphasizing the characteristics that makes it a member of a given class rather than another (FIG. 4). However, the peculiar feature that distinguishes neural networks from other types of classifiers, is that the former are able to make these features abstract through a set of examples, without these having to be specified a priori. During this step, called training, the network assigns for each example the probability that it belongs to a certain class rather than another. If the classification has been successful, the class associated with the highest probability will coincide with the actual class to which the object belongs.

However, this condition is reached only possibly at the end of the learning step, during which the synaptic connections of the network are modified in such a way as to minimize a cost function that contains information on the number of incorrectly classified examples. In the specific case of cyst classification, one of the most used in Machine Learning was chosen as the cost function, namely the cross-entropy function:

$$L(p, q) = -\sum_{\mu=1}^{M}\sum_{c=1}^{C} p_\mu(c) \log q_\mu(c; W),$$

where M indicates the number of examples, p the effective probability that an example μ belongs to the class c and q the probability that an example μ belongs to the class c, however assigned by the network on the basis of the current configuration of its synaptic connections W.

The cost function is optimized by means of optimization algorithms, such as for example Gradient Descent (GD) and its variants. These algorithms provide the prescription, or the learning rule, through which the network connections must be modified in such a way as to allow it to correctly classify the whole set of examples. In particular, in the case of the GD and its variants, the synaptic connections are updated along the direction of the gradient:

$$W \leftarrow W + \eta \frac{\partial L(p, q)}{\partial W}$$

where η determines the update step and is therefore called the learning rate. In particular, the use as an optimization algorithm of the variant known as Adam was tested, in which the learning rate instead of remaining constant throughout the training and the same for each synaptic connection, is adapted based on the first and second momentum of the gradient.

To improve the performance of the network in general, there are functions that can prevent overfitting on training examples, such as dropouts.

It is also possible to use convolutional feed-forward networks. In an initial phase of the project, it was decided to successfully implement a simpler type of feed-forward network, namely the Perceptron multilayer. In the preferred but non-limiting case in which the ultrasound scan is classified as containing a serous cyst, it is possible, with appreciable results, to locate it and automatically extract some geometric characteristics. Specifically, the two steps of localization and geometric characterization are preferably approached with computational graphics techniques. Alternatively, localization can be performed by a neural network, in particular by a convolutional neural network. Preferably, with reference to localization, in order to localize the position of the serous cyst, several complexities must be taken into account, including:

Multilocular cyst: it is common for the cyst to present several loculi and the potential presence of more than one serous area should be taken into account;

Serum and Mucin: the serum must also be identified in the presence of mucus;

Visually similar ultrasound areas that do not represent serous cysts. It is necessary to distinguish between generic dark parts and dark parts that actually represent the cyst serum.

Figure 5:
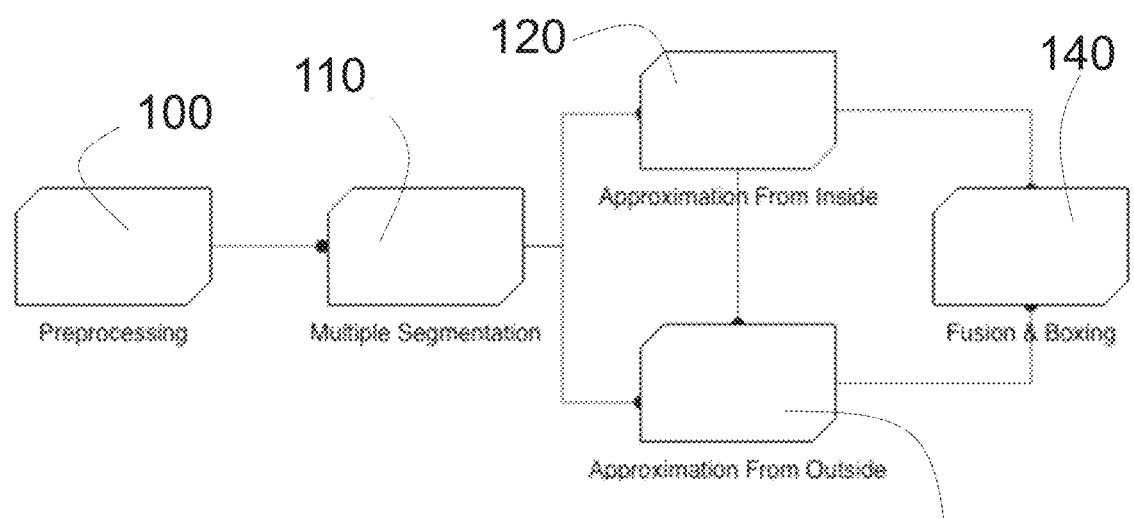
FIG. 5 is a simplified block diagram of a computer graphics process performed by the method of the present invention.

To take all these elements into consideration, an approach is applied (FIG. 5) that approximates the cyst from the inside and from the outside; that is, it aims to recognize the serous (internal) components and the boundary tissues. This is useful since the serous component alone may not be totally indicative of pathologies and, in general, the boundary tissues represent an important element for evaluating the state of the cyst.

In the preprocessing step 100 an ultrasound cropping is performed so as to eliminate unnecessary portions of the ultrasound, such as rasterized metadata with the actual ultrasound image (e.g. patient registry, echo scale in mm). The entropy of the image is then calculated by means of an entropic filter (FIGS. 6A and 6B) in order to make more evident the areas whose gray levels are homogeneous, Indicatively this makes the serous areas and the surrounding tissues more visible, when actually visually homogeneous. Alternatively, it is possible to apply filters to Hessian matrices.

Subsequently, the crop of the entropic image is binarized through specific thresholds and then segmented 110 in order to extract three different segmentations. Two of these (FIGS. 7A, 7B) represent an approximation of the serous zone with respective different but both low thresholds to identify the areas with high contrast and low entropy, the remaining instead the boundary tissues (FIG. 7C) through the application of a high threshold, i.e. to identify areas with high entropy. The two approximations of the serous zone, therefore internal to the cyst, have slightly different visual characteristics and are useful for validating the results. In particular, the two internal segmentations differ in that the respective thresholds adopted for binarization have similar but not identical values.

Specifically, taken the two segmentations from the inside, the centroids of the connected dark components are calculated, i.e. the closed areas representing the serous areas, of an image (FIG. 8A) and a check is made that they are contained within the connected components of the other segmentation with low threshold. When this and other conditions have occurred, e.g. connected component area above a predetermined and adjustable threshold, distant connected component, e.g. outside a predetermined and adjustable limit distance, from the boundaries of the echo graphic image, and a predetermined and adjustable form factor on the basis of the relationship between a major axis and a minor axis of the component connected approximated with an ellipse, then the components are considered connected as actually representing a serous zone (FIG. 8B).

When the roughness of the perimeters of the identified areas is also considered, a relatively high value, e.g. beyond an adjustable threshold, is associated with the presence of papillae. It is understood that the roughness and related quantities such as local peak, local valley, reference line, peak and valley, can be calculated at the perimeter of a connected area, preferably of a binary image, in the same way as it happens to the surface of a body.

In this way it is possible to locate a number of serous zones as desired, the maximum number of which is defined by means of a specific modifiable parameter; consequently the method of the present invention is capable of identifying multilocular cysts and locating their individual loculi. The external segmentation 130, that is, the one that identifies the contours of the cyst, must be compared with the serous areas actually identified and selected in step 120. Preferably, only the contours sufficiently close to the serum are selected. To calculate the distance between the boundary tissues and the serous area, the Euclidean distances between the centroids of the serous zones (FIG. 8B) and those of the individual segmented boundaries (FIG. 9A) are considered: if this distance is less than a predefined and adjustable threshold, the examined boundary is associated with the zone and therefore selected (FIG. 9B). The default threshold can be fixed or adaptive, i.e. be expressed as a function of the size of the serous zone, for example of one or both of the half axes. In this way each frame will be associated with its boundaries.

Once both the serous areas and the relative boundaries have been extracted, this information is merged into a single image 140. This eases the visual identification of the areas of interest and enables easier reading of the ultrasound scan.

To further ease the reading of the ultrasound image, the method of the present invention includes the step of calculating some geometric properties of the cyst. Specifically, all the measures are calculated which, in themselves, are calculated in a known way and not further described. For clarity, the most useful and significant ones are:

Minor and major axes of the ellipse most similar to the identified area: they represent a good estimate of measurement (in pixels) of the width and height of the cyst.

Orientation: i.e. the angle between the horizontal reference axis of the image and the major axis.

Centroid: the center of gravity of the identified area.

Cyst area: measured in pixels, it approximates the effective extent of the cyst.

Figure 10:
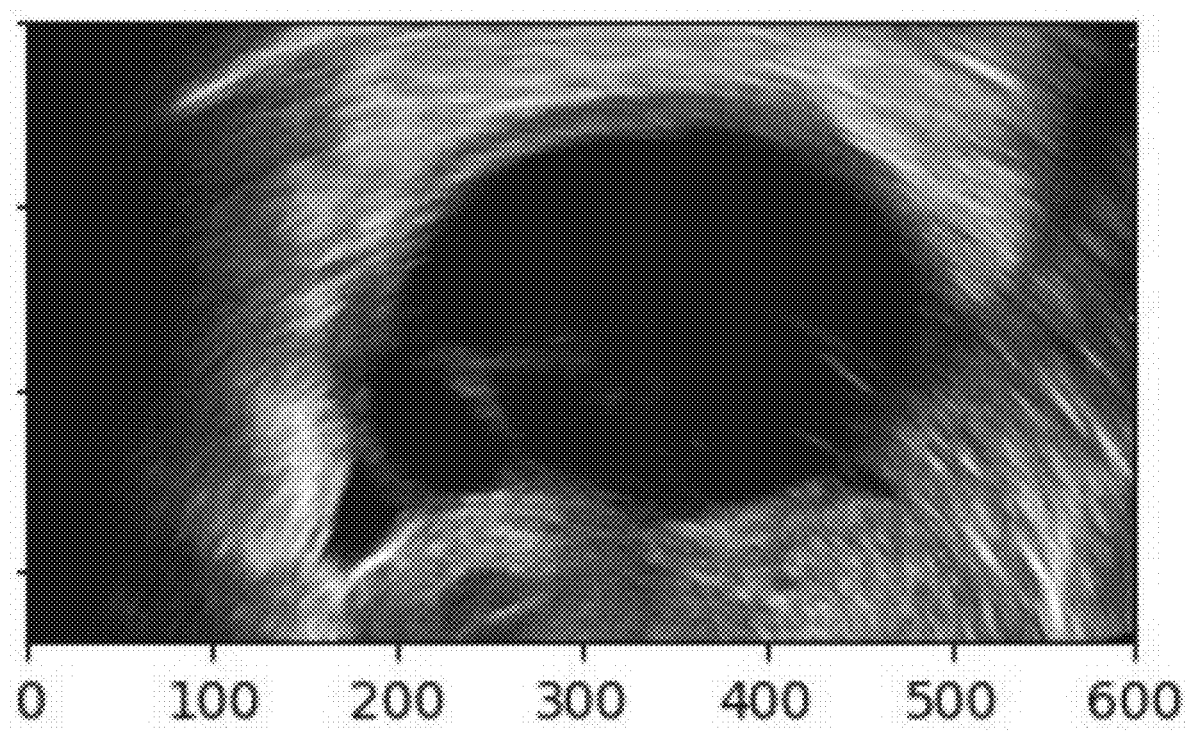
FIG. 10 is an enlargement of FIG. 6A; is
Figure 11:
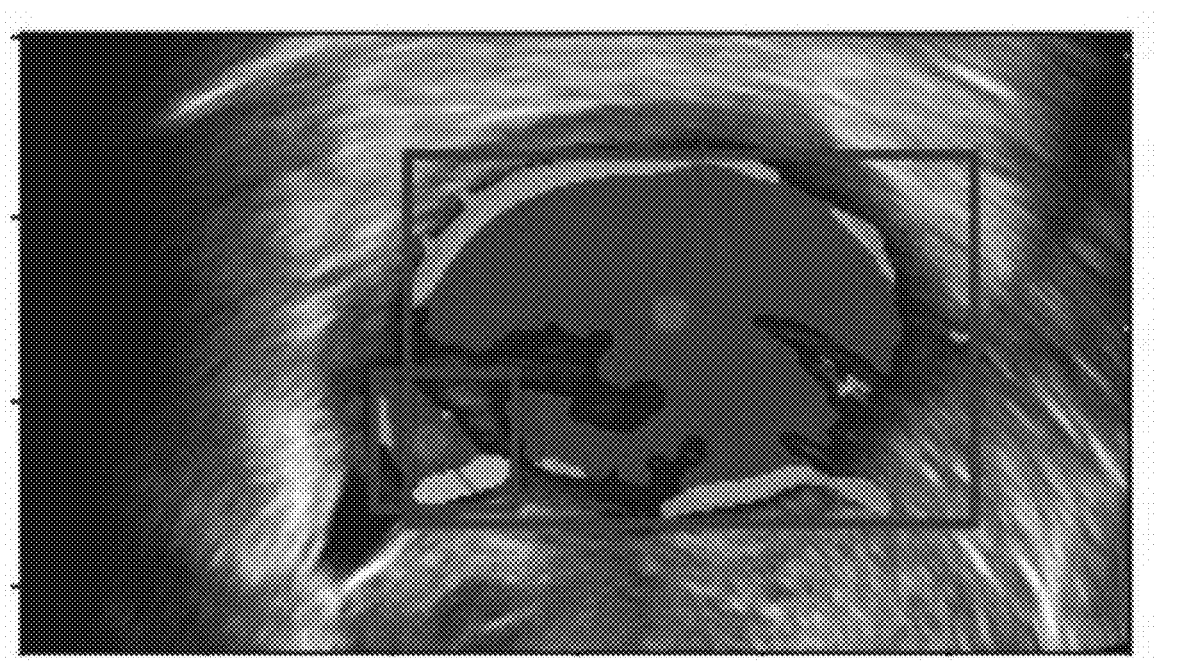
FIG. 11 is an example of output of the process of FIG. 5 applied to FIG. 6A.

FIGS. 10 and 11 respectively illustrate a captured ultrasound image and the result of the graphic processing of the method according to the present invention.

The previous paragraphs refer to the application of the method according to the present invention to a single ultrasound image.

According to the present invention, it is also possible to process the frames of an ultrasound clip as follows.

Each frame of the clip is labeled so as to associate a numerical label for each individual frame that makes up the clip. The clip is then associated with a list that reports the numeric label for each frame that composes the video and each image is processed as described in the preceding paragraphs so that the list provides, for each frame identified by a label, the relative class and subclass.

The list is subsequently processed in order to provide an overall classification of the cyst represented by the frames, whereas some frames may not include a cyst, that instead is present in other frames.

For this purpose, in order to classify the cyst to which the clip refers, multilocular sub-classification prevails over unilocular sub-classification, i.e. if at least one frame of the clip is multilocular, the cyst is classified as multilocular. Similarly, if at least one frame is classified as solid, this class prevails to describe the cyst if other frames are classified as serous.

Furthermore, the counting of the frames can also be performed by storing the position of the centroids of each loculum for each frame. If in a frame a centroid of a loculum has a greater distance than a predetermined threshold compared to other centroids of other loculi, this loculum is considered as an additional loculum and not as a loculum already present in other frames and therefore the total number of loculi is updated accordingly,

What is claimed is:

1. A computer based method for finding and characterizing an anatomic mass of an organ as a cyst and providing a class indicating a presence of a serum in the cyst and a sub-class indicating a presence of one or more serous loculi in the cyst and/or a number of the one or more serous loculi in the cyst, comprising:

(a) obtaining at least an ultrasound image of an examined anatomic entity comprising the anatomic mass;

(b) using a first algorithm based on a neural network elaborating the ultrasound image for outputting a characterization as the cyst and/or the class of the cyst;

(c) using a second algorithm of computational graphics for:

i. identifying inner regions of the ultrasound image, each of said inner regions being a fluid region or a boundary region, based on at least a first threshold and a second threshold applied to a mathematical function of an echogenicity of the ultrasound image;

ii. classifying each inner region as a serous region or a solid region based on a quantitative morphologic parameter of the each inner region and on an aggregation model generating an association between at least a fluid internal region and a boundary internal region when a proximity condition is verified between the fluid internal region and the boundary internal region;

iii. counting a number of serous regions as the one or more serous loculi and/or a number of solid regions;

(d) providing an image classification comprising the class and the sub-class based on a combination of outputs from the first algorithm and the second algorithm.

2. The computer based method according to claim 1, wherein the identifying inner regions of the ultrasound image comprises associating to an identical anatomical entity, wherein the identical anatomical entity comprises the cyst, at least a subset of the inner regions based on a distance between relative centroids.

3. The computer based method according to claim 2, wherein the obtaining at least an ultrasound image comprises obtaining a multiframe clip of ultrasound images of the anatomic mass and providing an overall class or sub-class of the multiframe clip, wherein a multilocular prevails over an unilocular and/or a solid prevails over a serous when a first sub-class of a first frame and a second sub-class of a second frame image of the multiframe clip have different outputs from the providing the image classification.

4. The computer based method according to claim 3, wherein the using the second algorithm comprises outputting the number of the one or more serous loculi as a part of the sub-class.

5. The computer based method according to claim 1, wherein the using the second algorithm comprises comparing an overall area of the serous regions and an overall area of the solid regions, and the providing the image classification comprises indicating the sub-class based on the comparing.

6. The computer based method according to claim 1, wherein in the using the second algorithm, the serous regions and boundary regions around the serous regions are identified as first respective geometrical features, relative centroids are calculated as second respective geometrical features and positions of the relative centroids are calculated as respective quantitative parameters.

7. The computer based method according to claim 6, wherein in the using the second algorithm, a relative centroid is associated to a given serous region based on a predefined maximum distance between the relative centroid of the serous region and the relative centroids of the boundary regions.

8. The computer based method according to claim 1, wherein in the using the second algorithm, an entropic filter or a Hessian matrix filter is applied to the ultrasound image to increase a differentiation between fluid regions surrounding a boundary solid region.

9. The computer based method according to claim 1, wherein the neural network is either a feed-forward convolutional network or a feed-forward multilayer network.

10. The computer based method according to claim 1, wherein both the first algorithm and the second algorithm output both a serous classification or a solid classification and a unilocular sub-classification or a multilocular sub-classification and wherein, in the providing the image classification, the outputs of the first algorithm and the second algorithm are identical.

11. The computer based method according to according to claim 1, wherein the second algorithm is selected from a group consisting of an edge extraction algorithm, a region extraction algorithm and an image description of properties algorithm.

\* \* \* \* \*